US008715436B2

(12) United States Patent
Bhatia et al.

(10) Patent No.: US 8,715,436 B2
(45) Date of Patent: May 6, 2014

(54) MICROFABRICATED BIOPOLYMER SCAFFOLDS AND METHOD OF MAKING SAME

(75) Inventors: Sangeeta N. Bhatia, La Jolla, CA (US); Giovanni Vozzi, Eboli (IT)

(73) Assignee: The Regents of the University of California, Oakland, CA (US)

( * ) Notice: Subject to any disclaimer, the term of this patent is extended or adjusted under 35 U.S.C. 154(b) by 1157 days.

(21) Appl. No.: 10/750,293

(22) Filed: Dec. 31, 2003

(65) Prior Publication Data
US 2005/0008675 A1      Jan. 13, 2005

Related U.S. Application Data (63) Continuation of application No. PCT/US02/21207, filed on Jul. 2, 2002.

(60) Provisional application No. 60/302,879, filed on Jul. 3, 2001.

(51) Int. Cl.
*A61F 2/00* (2006.01)
*B29C 65/00* (2006.01)
*B32B 3/10* (2006.01)

(52) U.S. Cl.
USPC ............ 156/77; 424/423; 424/424; 424/425; 424/426; 428/131; 428/137; 428/220; 428/332; 428/339; 156/137

(58) Field of Classification Search
USPC .......... 424/423, 424, 425, 426; 428/131, 220, 428/332, 339, 137; 156/77
See application file for complete search history.

(56) References Cited

U.S. PATENT DOCUMENTS

| | | | |
|---|---|---|---|
| 5,443,950 | A | 8/1995 | Naughton et al. |
| 5,486,546 | A | 1/1996 | Mathiesen et al. |
| 5,514,378 | A | 5/1996 | Mikos et al. |
| 5,776,748 | A | 7/1998 | Singhvi et al. |
| 6,039,897 | A | 3/2000 | Lochhead |
| 6,103,255 | A | 8/2000 | Levene |
| 6,143,293 | A | 11/2000 | Weiss |

(Continued)

FOREIGN PATENT DOCUMENTS

| | | | |
|---|---|---|---|
| EP | 1 027 897 A1 | * | 8/2000 |
| WO | WO 2004/026115 A2 | | 4/2002 |

(Continued)

OTHER PUBLICATIONS

Bhatia SN, and Chen C (1999) Tissue Engineering at the Micro-Scale, Biomedical Microdevices 2:131-144.

(Continued)

*Primary Examiner* — Leo B Tentoni
(74) *Attorney, Agent, or Firm* — Nelson Mullins Riley & Scarborough LLP; Debra J. Milasincic, Esq.

(57) ABSTRACT

The invention is a series of soft lithographic methods for the microfabrication of biopolymer scaffolds for use in tissue engineering and the development of artificial organs. The methods present a wide range of possibilities to construct two- and three-dimensional scaffolds with desired characteristics according to the final application. The methods utilize an elastomer mold which the biopolymer scaffold is cast. The methods allow for the rapid and inexpensive production of biopolymer scaffolds with limited specialized equipment and user expertise.

16 Claims, 4 Drawing Sheets

(56) References Cited

U.S. PATENT DOCUMENTS

| | | | |
|---|---|---|---|
| 6,160,084 | A | 12/2000 | Langer et al. |
| 6,203,573 | B1 | 3/2001 | Walter et al. |
| 6,337,198 | B1 * | 1/2002 | Levene et al. ............... 435/174 |
| 6,379,962 | B1 | 4/2002 | Holy et al. |
| 6,423,252 | B1 | 7/2002 | Chun et al. |
| 6,790,455 | B2 * | 9/2004 | Chu et al. ............... 424/423 |
| 6,872,387 | B1 * | 3/2005 | Ma ............... 424/93.21 |
| 2001/0043918 | A1 * | 11/2001 | Masini et al. ............... 424/93.7 |
| 2002/0127711 | A1 * | 9/2002 | Kale et al. ............... 424/423 X |
| 2006/0014358 | A1 | 1/2006 | Sawyer et al. |
| 2006/0136182 | A1 | 6/2006 | Vacanti et al. |
| 2007/0148139 | A1 | 6/2007 | Vacanti et al. |

FOREIGN PATENT DOCUMENTS

| | | | |
|---|---|---|---|
| WO | WO 02/053193 | A2 | 7/2002 |
| WO | WO 03/082145 | A2 | 10/2003 |
| WO | WO 2005/034624 | A2 | 4/2005 |
| WO | WO 2005/060396 | A2 | 7/2005 |

OTHER PUBLICATIONS

Bhatia, S.N., Balis U, Yarmush ML, and Toner M, Effect of Cell—Cell interactions in preservation of cellular phenotype: Co-Cultivation of Hepatocytes and Non-Parenchimal Cells, FASEB J, (1999), 13(14): p. 1883-1990.

Borenstein J.T., Terai H, King K.R., Weinberg E.J., Kaazempur-Mofrad M.R., and Vacanti J.P. Microfabrication Technology for Vascularized Tissue Engineering. Biomedical Microdevices, 2002 (4:3) p. 167-175.

Chu TM, Orton DG, Hollister SJ, Feinberg SE, and Halloran JW. (2002) Mechanical and in vivo performance of hydroxyapatite implants with controlled architectures.Biomaterials, 23:1283-1293.

Hermanson, G.T. (1996) Bioconjugate Techniques. Academic Press.

Kapur R, Spargo BJ, Chen MS, Calvert JM, Rudolph AS (1996) Fabrication and selective surface modification of 3-dimensionally textured biomedical polymers from etched silicon substrates, J Biomed Mater Res. 33:205-16.

Mikos A.G., Sarakinos G., Leite S.M., Vacanti J.P., Langer R. (1993) Laminated three-dimensional biodegradable foams for use in tissue engineering, Biomaterials 14:323-330.

Mrksich, M., at al.. (1997) Using microcontact printing to pattern the attachment of mammalian cells to self-assembled monolayers of alkanethiolates on transparent films of gold and silver. Experimental Cell Research 235:305-13.

Park A, Wu B, Griffith LG (1998) Integration of surface modification and 3D fabrication techniques to prepare patterned poly(L-lactide) substrates allowing regionally selective cell adhesion, J Biomater Sci Polym Ed. 9:89-110.

Shastri VP, Martin I, Langer R. (2000), Macroporous polymer foams by hydrocarbon templating. Proc Natl Acad Sci USA. 97:1970-5.

Zein I, Hutmacher DW, Tan KC, Teoh SH. (2000) Fused deposition modeling of novel scaffolds archtectures for tissue engineering applications. Biomaterials 23:1169-1185.

Zhao B., Moore J.S.,. Beebe D.J. (2001) Surface-directed liquid flow inside microchannels. Science 291: 1023.

Bhatia et al., "Micropatterning Cells in Tissue Engineering" Methods in Molecular Medicine, vol. 18, pp. 349-363.

Bhatia et al., "Controlling Cell interactions by Micropatterning in Co-Cultures: Hepatocytes and 3T3 Fibroblasts" Journal fo Biomedical Materials Research, vol. 34, 189-1999 (1997).

* cited by examiner

MICROFLUIDIC MOLDING

INVERT MOLD,
SEAL TO SURFACE.
PERFUSE PLGA SOLUTION
BY APPLYING
NEGATIVE PRESSURE

BAKE MOLD + PLGA

PEEL PDMS
FROM SURFACE

FIG. 3

SPIN COATING

APPLY PLGA SOLUTION
TO PDMS MOLD,
SPIN AT 2000 RPM

BAKE MOLD + PLGA

PEEL SCAFFOLD
FROM MOLD

MICROFABRICATED BIOPOLYMER SCAFFOLDS AND METHOD OF MAKING SAME

CROSS-REFERENCES TO RELATED APPLICATIONS

This application is a continuation and claims priority under 35 U.S.C. §120 to International Application Serial No. PCT/US02/21207 filed Jul. 2, 2002, which claims priority from U.S. Provisional Application Ser. No. 60/302,879, filed Jul. 3, 2001.

GOVERNMENT INTEREST

The invention was made with government support from the National Institutes of Health under grant number 5 RO1 DK56966-02.

BACKGROUND OF THE INVENTION

Tissue engineering describes an attempt to create tissues that repair or replace damaged tissues, typically by combining the use of biomaterials and cells. Control of polymer scaffold architecture is of fundamental importance in tissue engineering A wide variety of techniques for controlling the architecture of biomaterials are already available for relatively large feature sizes of the order of millimeters to centimeters. These include polymer extrusion, solution casting and particulate leaching, deposition of a polymer solution stream on a spinning mandrel and manipulation of sheets of polymer meshes. To achieve arbitrary three-dimensional geometries, preformed sheets of biomaterial have been cut and laminated with a resolution of 0.5 mm. Such supports are useful for forming the macroscopic shape of the replacement tissue (i.e. an ear for cartilage tissue engineering) or for customizing tissues replacements for individualized patients (i.e. an eye socket for bone tissue engineering).

To manipulate scaffold architecture on smaller length scales, many different microfabrication techniques have been developed in recent years, each with its own intrinsic limits related to the materials employed, its resolution or its costs. Injection molding against a microfabricated silicon template was utilized by Kapur et al (1996) with a resolution of 10 microns. In addition, a three dimensional printing technique developed by Griffith et al (1998) utilizes a polymer powder spread on a plate. Three dimensional structures are achieved by application of a solvent binder (e.g. chloroform) through an ink-jet head (Shastri et al., 2000). The resolution of this method is dependent upon the polymer particle size where the typical features are on the order of 300 microns. These techniques are useful for forming complex tissues such as bone/cartilage composites for the knee and for optimizing microscale architecture to improve the function of the resultant tissue. For example, scaffold texture can alter cell migration, ingrowth, vascularization, and host integration. Microscale scaffold architecture can also modify the cellular responses such as growth and differentiation as has been shown on three-dimensional polymer meshes (e.g. U.S. Pat. No. 5,443, 950) Many of the techniques described above require processing conditions such as heating and polymer grinding that may be limiting for the inclusion of bioactive moieties or high resolution features, respectively.

Methods to prepare scaffolds with microscale structure that are more amenable to use with biodegradable polymers such as poly-DL-lactide-co-glycolide (PLGA) have also been developed. Material microstructure was first controlled by process parameters such as the choice of solvent in phase separation, doping with particulate leachants, gas foaming, woven fibers, and controlled ice crystal formation and subsequent freeze-drying to create pores; however, these scaffolds lack a well-defined organization that is found in most tissues in vivo (i.e. pores are randomly distributed rather than oriented and organized in functional units).

At the microscale, techniques to control the architecture of biodegradable polyester scaffolds, such as poly(DL-lactide-co-glycolide) (PLGA), are being developed and described in the literature. For example, a Fused Deposition Modelling (FDM) method can create solid objects with ~250 micron resolution using a robotically controlled miniature extruder head (Zein et al, 2000). Biodegradable polymer membranes of thickness between 500 and 2000 microns cut by laser can be laminated to produce structures with 100 micron resolution (Mikos et al., 1993). By exploiting computer-aided design and solid free form fabrication, both three-dimensional printing and lost mold methods have been developed. Three dimensional printing employs polyester particles that are bound together by the application of chloroform from an inkjet head with a resolution of approximately 300 microns (Mrksich et al., 1997). Similarly, the lost mold technique uses stereolithography to fabricate an epoxy mold that is lost when the surrounding ceramic is heated, with a resolution of approximately 450 microns (Chu et al, 2002). Although complex objects can be created using these various technologies, the ability to reproducibly and simply fabricate polyester scaffolds with organized, arbitrarily-oriented tissue-scale features (i.e. 10-100 microns) has not been reported.

SUMMARY OF THE INVENTION

The invention is a series of soft lithography microfabrication methods for the generation of two- and three-dimensional polymer scaffolds. These methods present a wide range of possibilities to construct scaffolds with the desired characteristics according to the final application. The methods utilize a mold comprised of a polymeric material, preferably a silicone elastomer, (e.g. those described in U.S. Pat. No. 5,776,748, incorporated herein by reference) cast on a silicon master. The silicon master is generated by patterning of thick photoresist SU-8™ directly with light through an inexpensive transparency and requires no reactive ion etching. The silicon elastomer mold is used as a template on which the polymer (e.g. those described in U.S. Pat. No. 6,160,084, incorporated herein by reference) scaffold is cast. The silicon elastomer mold is flexible and may be deformed into any of a number of shapes including tubes. The methods of the invention allow for the relatively rapid microfabrication of scaffolds with minimal specialized equipment making the process relatively inexpensive and allowing for fabrication of scaffolds by users without substantial specific expertise. Additionally, the short turnaround time of 1-2 days from design of a mask to production of a polymer scaffold allows for rapid, iterative experimentation to produce optimal scaffolds. The method of the invention further comprises the assembly of two-dimensional membranes into three-dimensional scaffolds by membrane lamination (i.e. stacking). The two-dimensional membranes can be adhered to each other with poly(dimethylsiloxane) (PDMS) or by the application of mechanical pressure to the layered scaffolds after assembly.

The invention is the two- and three dimensional scaffolds manufactured by the soft lithography microfabrication and lamination methods of the invention. The scaffolds may be modified by any of a number of methods for use in a variety of applications. The size and shape of the scaffolds is limited only by the limitations of the microfabrication methods and are not limited to scaffolds for any particular use.

The invention is the use of the two- and three dimensional scaffolds manufactured by the soft lithography microfabrication methods of the instant invention for the growth of cells. The scaffolds may be used for growth of homogeneous or heterogeneous cell populations. The scaffolds may be coated homogeneously or heterogeneously with collagen or other extracellular matrix or biomolecules to facilitate adhesion and promote growth of cells. Cells may be grown on scaffolds for use in laboratory settings or in the preparation of artificial organs for apparatus for use outside of the body or for transplant of the cells affixed to the scaffold into the body. Such 'tissue engineered' constructs may also be useful for forming miniaturized tissues for pharmaceutical drug development and high-throughput screening or for controlling the differentiation of cells (stem cells or adult cells) through control of the microenvironmental 'niche'.

The present invention will be better understood from the following detailed description of an exemplary embodiment of the invention, taken in conjunction with the accompanying drawings.

DETAILED DESCRIPTION AND PREFERRED EMBODIMENT

The fabrication of three-dimensional scaffolds that mimic the in vivo cellular microenvironment is of fundamental importance to the success of tissue engineered constructs. Both scaffold chemistry and architecture can influence the fate and function of engrafted cells. While several different techniques have been developed to control scaffold architecture, each method has intrinsic limits related to the resolution, necessary infrastructure, or versatility. Molding of PLGA networks directly from microfabricated silicon masters has been previously reported (Borenstein et al., 2002); however, the technique was not extensively characterized with regard to polymer concentration, mold release conditions, and other process parameters. Moreover, molding of PLGA networks from PDMS masters was not described. The invention is three soft lithography methods that utilize elastomer masters to allow for the production of two- and three-dimensional scaffolds composed of a polymer for use in a variety of tissue engineering applications. Elastomers have some advantages over the use of silicon molds. The molds are inexpensive and reuseable. They do not require chemical and wet etching as silicon molds do. Etching methods require specialize equipment and skills. Elastomer molds can be sealed to glass or other solid supports which is essential for the microfluidic molding method. Additionally, elastomer molds are deformable allowing the membranes to be cast onto curved and tubular surfaces.

As used herein, the following terms will be understood to have the following definitions:

Elastomers refers to a variety of elastomeric polymeric materials that are suitable for fabrication of molds, especially polymers of the general classes of silicone polymers and epoxy polymers (such as those listed in U.S. Pat. No. 5,776, 748). Epoxy polymers are characterized by the presence of a three-member cyclic ether group commonly referred to as an epoxy group, 1,2-epoxide, or oxirane. For example, diglycidyl ethers of bisphenol A may be used, in addition to compounds based on aromatic amine, triazine, and cycloaliphatic backbones. Another example includes the well-known Novolac polymers. Examples of silicone elastomers suitable for use as the mold include those formed from precursors including the chlorosilanes such as methylchlorosilanes, ethylchlorosilanes, and phenylchlorosilanes, and the like. A particularly preferred silicone elastomer is polydimethylsiloxane (PDMS).

Polymer refers to a chemical compound or mixture of compounds formed by polymerization and consisting essentially of repeating structural units.

Biopolymer refers to a synthetic material used in a medical device or an in vivo or in vitro culture system that is intended to interact with a biological system. Biopolymers include, but are not limited to those taught in U.S. Pat. No. 5,514,378 (incorporated herein by reference). These biodegradable polymers include lactic acid polymers such as poly(L-lactic acid) (PLLA), poly(DL-lactic acid) (PLA), and poly(DL-lactic-co-glycolic acid) (PLGA). The co-monomer (lactide: glycolide) ratios of the poly(DL-lactic-co-glycolic acid) are preferably between 100:0 and 50:50. Most preferably, the co-monomer ratios are between 85:15 (PLGA 85:15) and 50:50 (PLGA 50:50). Blends of PLLA with PLGA, preferably PLGA 85:15 and PLGA 50:50, are also used to prepare polymer membranes. Other representative polymers include polyorthoesters, and although not preferred for mechanical characteristics, polyanhydrides. The preferred biodegradable polymers are all degraded by hydrolysis. It is possible, however, to use other materials which degrade enzymatically. Reagents can be purchased from any of a number of commercial sources well known to those skilled in the art. Other polymers include polymers in the form of a hydrogel (typically absorbing up to about 90% by weight of water), and can optionally be ionically crosslinked with multivalent ions or polymers. Ionic crosslinking between soft segments can be used to hold a structure, which, when deformed, can be reformed by breaking the ionic crosslinks between the soft segments. The polymer may also be in the form of a gel in solvents other than water or aqueous solutions. In these polymers, the temporary shape can be fixed by hydrophilic interactions between soft segments. Hydrogels can be formed from polyethylene glycol, polyethylene oxide, polyvinyl alcohol, polyvinyl pyrrolidone, polyacrylates, poly (ethylene terephthalate), poly(vinyl acetate), and copolymers and blends thereof. Several polymeric segments, for example, acrylic acid, are elastomeric only when the polymer is hydrated and hydrogels are formed. Other polymeric segments, for example, methacrylic acid, are crystalline and capable of melting even when the polymers are not hydrated. Either type of polymeric block can be used, depending on the desired application and conditions of use.

Membrane refers to a single, two-dimensional product composed of a polymer made by any of the soft lithography methods of the invention. Membranes may be continuous structures or have through-holes Scaffold refers to a two- or three-dimensional product composed of a polymer made by the soft lithography methods of the invention.

Coating substance refers to cell adhesion molecules that promote or inhibit cell adhesion which include, but are not limited to biomolecules, peptides and proteins and polysaccharides. More specifically molecules to promote cell adhesion include collagen, fibronectin, vitronectin, RGD (Arg-Gly-Asp) and YIGSR (Tyr-Ile-Gly-Ser-Arg) peptides, glycosaminoglycans (GAGs), hyaluronic acid (HA), integrins, selectins and cadherins. Molecules to inhibit cell adhesion include triblock polymers such as pluronic. Such polymers may be further modified with specific adhesive peptides or proteins. Triblock polymers, with or without modification, may be applied selectively to coat the scaffolds to promote site specific attachment of the cells. Such methods are well known to those skilled in the art (e.g. see Hermanson, 1996).

Lamination refers to uniting layers of material. In the present invention, lamination specifically refers to uniting polymer membranes by an adhesive, pressure or other means to form three-dimensional structures.

Particles used for particulate leaching may be any salt that forms crystals or particles having a diameter less than 500 microns, which is easily removed from and does not react with the polymer, and is non-toxic if some residue remains in the polymer after leaching such as those described in U.S. Pat. No. 5,514,378. Examples are proteins such as gelatin and agarose, starches, polysaccharides and sugars such as alginate and other polymers. Preferably, the salt is a sodium salt, such as sodium chloride, sodium tartrate and sodium citrate, and other water soluble salts or compounds not soluble in the polymer solvent, for example, chloroform or methylene chloride. The most preferred salt is sodium chloride.

Soft lithography is the use of polymer molds in conjunction with photolithography.

Varying topology refers to surfaces that have variations in height.

Figure 1:
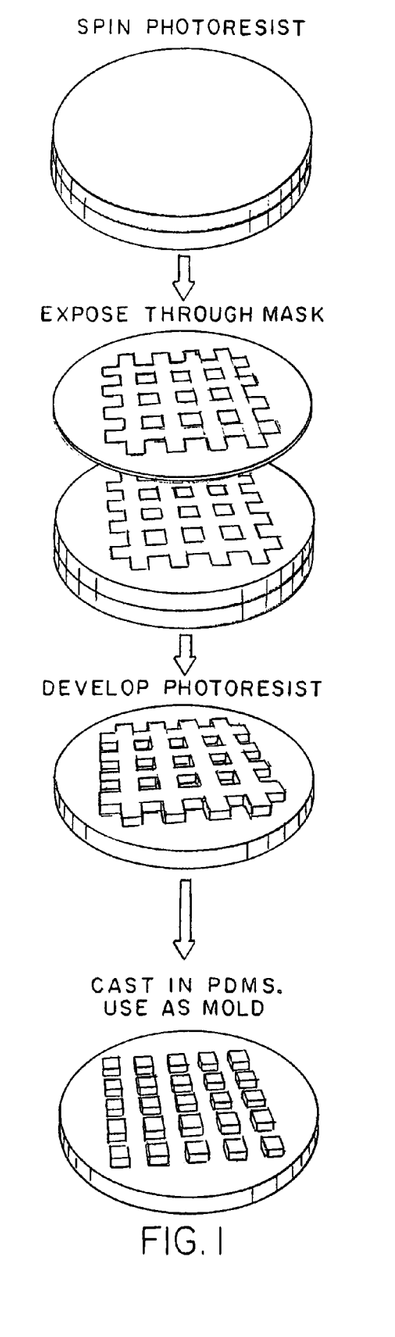
FIG. 1. Schematic illustration of the method of fabrication of PDMS molds.

The first step in the production of biopolymer scaffolds by any of the soft lithography methods of the invention is the production of a silicon template that allows the fabrication of the elastomer mold (FIG. 1). The PLGA mold was cast from a microfabricated silicon master using methods previously described (Zhao et al., 2001). Briefly, silicon 100 wafers were spin-coated with EPON-SU8™ photoresist (Microchem Co., Newton, Mass.), baked to drive away the solvent, and then exposed to UV light in a Bottom Side Mask Aligner (Karl Suss, Waterbury Center, Vt.) through a mask. The mask was created using Coreldraw 9.0 and printed on a transparency using a commercial Linotronic-Hercules 3300 dpi high-resolution line printer. Exposed photoresist was then developed (SU8 developer, Microchem Colo.) and subsequently the wafers were baked. PDMS prepolymer was prepared by mixing the commercially available prepolymer and catalyser (Sylgard 184 kit, Dow Corning) in a 10:1 w/w ratio. The mixture was degassed under vacuum to eliminate bubbles created during mixing. The prepolymer solution was cast on the master and placed under vacuum once again to remove any bubbles that may have been introduced. PDMS was cured by baking for two hours at 65° C. After cooling to room temperature, the PDMS was peeled from the silicon master. The mold was then washed with 70% ethanol and sonicated for 5 minutes prior to use.

Figure 2:
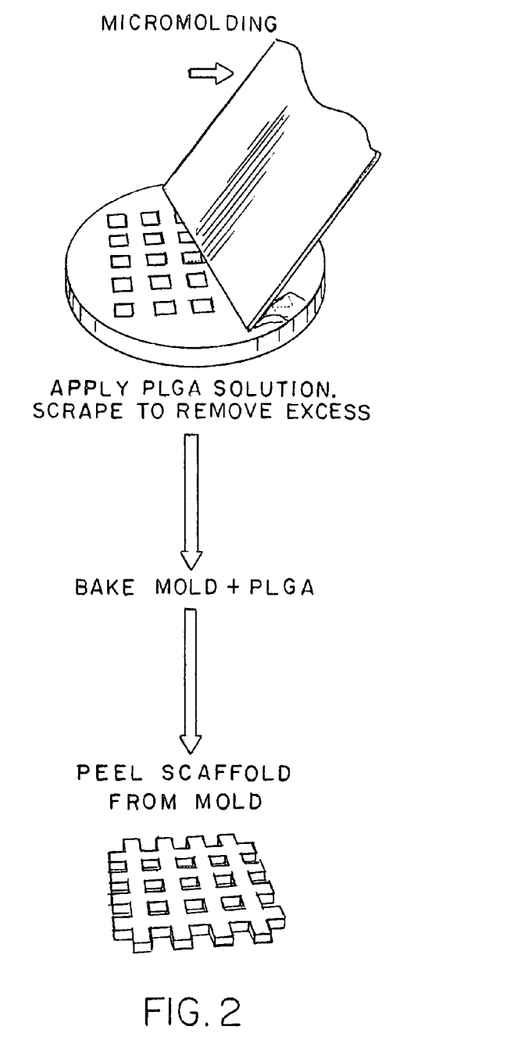
FIG. 2. Schematic illustration of the method of fabrication of membranes by micromolding.
Figure 3:
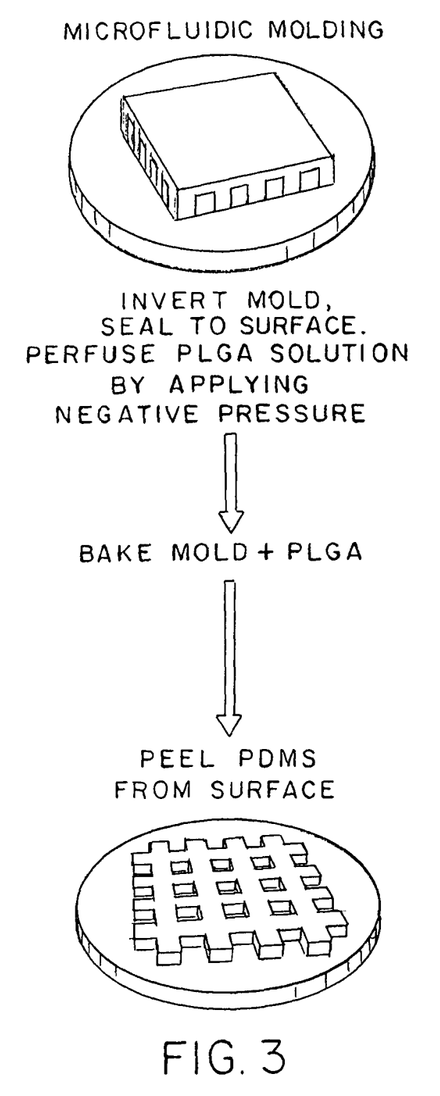
FIG. 3. Schematic illustration of the method of fabrication of membranes by microfluidics.
Figure 4:
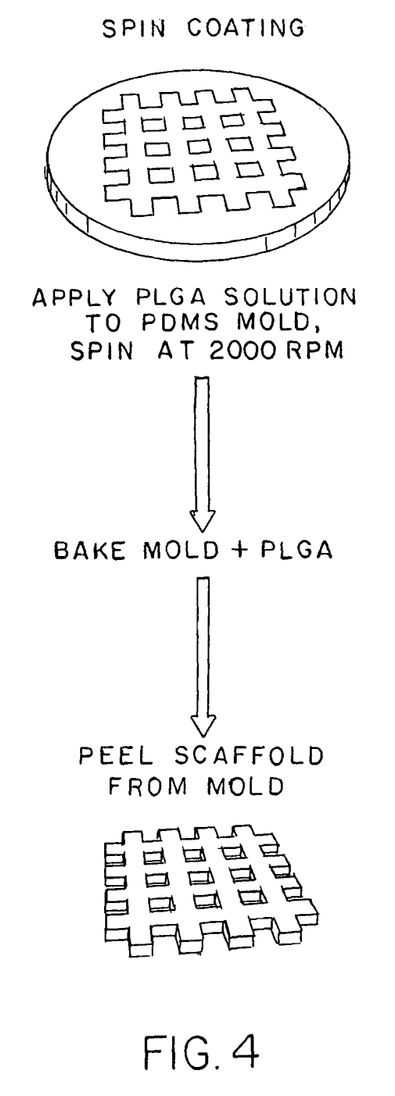
FIG. 4. Schematic illustration of the method of fabrication of by spin coating.

Once the PDMS master mold was obtained, casting of the membranes was performed in one of three ways, each with its own advantages and disadvantages. In the micromolding method, the polymer is cast on the mold under vacuum (FIG. 2). In the microfluidic method, a PDMS mold is sealed onto a desired substrate (e.g. glass, plastic) and the polymer solution is forced to flow through the channels by applying negative pressure (FIG. 3). In the spin-coating method, the polymer solution is spin coated onto the mold to allow the fabrication of thin membranes of non-uniform in height (FIG. 4). The selection of the method to be used depends on a number of factors including equipment available and the skills of the user. For example, preparation time for membranes prepared by spin-coating is less than for membranes prepared in by other methods. Microfluidics methods require the smallest amounts of user skill; however, the membranes cannot be used to assemble higher order structures as they are too tightly affixed to the substrate to allow for removal. Individual membranes made using the micromolding and microfluidic methods can be assembled into higher order structures using an optical microscope and tweezers. Higher order three-dimensional structures are constructed by layering membranes over each other using an optical microscope. Membranes are adhered to each other with PDMS, application of a thin layer of solvent to act as binder, or by applying a mechanical load to a set of PLGA membranes stacked together and heating for 10 minutes at 60° C.

Scaffold geometry of individual membranes and three-dimensional scaffolds was assessed by light and electron microscopy. The methods were all found to produce satisfactory and consistent results, although the membranes produced by each of the methods had characteristic properties. Specific times and polymer concentrations were found to be optimal with each of the methods. However, these parameters should not be considered limitations. The invention is the method for the preparation of the scaffolds which may be used with a variety of polymers and other scaffold materials.

Figure 5:
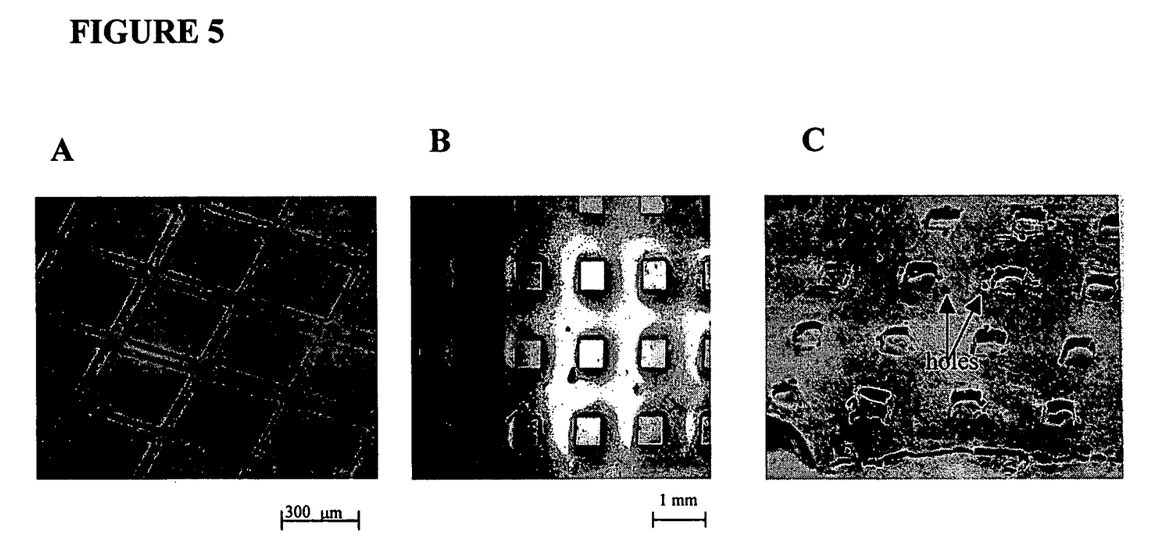
FIG. 5. Scaffolds produced by A) micromolding, B) microfluidics and C) spin coating.

Micromolding allows for the fabrication of patterns with a well-defined geometry with a resolution of about 20 microns. The thickness of the pattern is determined by the height of the features on the photolithographic master and by the concentration of the polymer solution. Typically, membranes were cast with a thickness of about 30 microns, however, it is possible to cast membranes with thicknesses from 1 micron to 1 mm. The solution wets the walls of the features, giving rise to menisci around each feature such that the top of the pattern is not flat. The optimal concentration of PLGA with this method is about 10-15%. The solution is viscous, usually around 100 Cp (SI units of viscosity-centipoise) which is enough to allow the solution to permeate the channels of the PDMS mold when placed under a vacuum. This method is most amenable to use when the area occupied by the polymer is larger than the spaces (e.g. 50 micron squares with gaps of 100 or more microns to the next nearest neighbor) (FIG. 5A). Membranes produced by this method can be laminated into higher order structures.

The microfluidic method allows for the fabrication of scaffolds with thin lines between spaces in the scaffold. The method exploits the sealing properties of PDMS and the capillary action of the microchannels present in the mold. This method results in the membrane being tightly adhered to the substrate making it difficult to remove without breaking. Therefore, scaffolds obtained by this method cannot be assembled into three-dimensional scaffolds. However, this method requires the least amount of user expertise and requires little specialized equipment (i.e. a vacuum pump and a PLGA mold). The method is limited in the size of the membrane that may be obtained based on the strength of the vacuum pump used. The average height is around 10 microns and the resolution of the method is dependent predominantly on the resolution of the PDMS mold. This method is most amenable to produce membranes with relatively wide portions of polymer between openings (e.g. 20-30 micron squares with gaps of 50 or more microns to the next nearest neighbor) (FIG. 5B).

The spin method allows for the microfabrication of scaffolds of a highly precise geometry using a solution containing a relatively low concentration of PLGA (e.g. 5%). Various rates of spinning and concentrations of PLGA allow for the production of scaffolds with various heights (e.g. 1 to 20). A velocity of 2000 rpm results in patterns with an average height of 7 microns. This method is limited to the production of scaffolds with line widths of about 100 microns as the polymer is not able to flow into microchannels. The method is also limited to scaffolds of a relatively small size (4 cm$^2$) as they are thin and fragile and may readily tear upon removal from the mold. This method is most amenable to produce membranes with relatively wide portions of polymer between openings (e.g. 50 micron squares with gaps of 100 or more microns to the next nearest neighbor) (FIG. 5C). Membranes produced by this method can be laminated into higher order structures.

Figure 6:
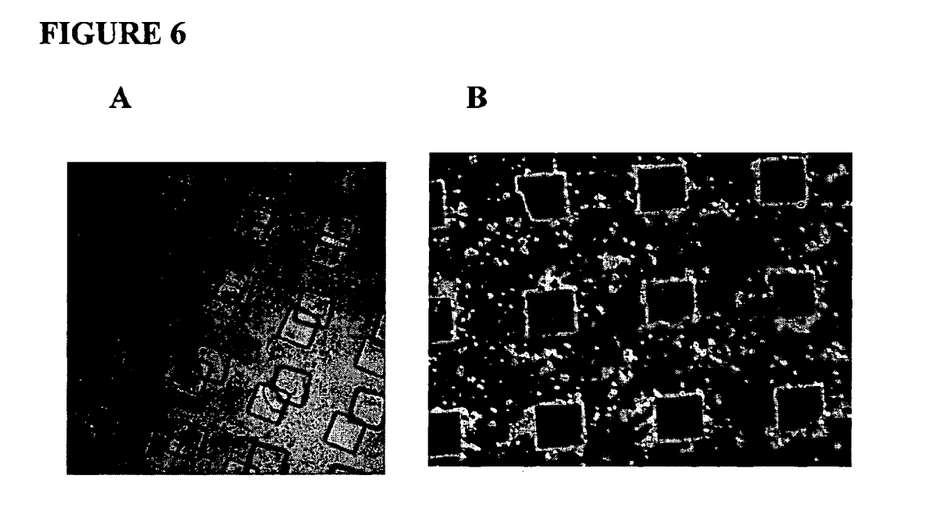
FIG. 6. A) Multilayer PLGA structure formed by thermal lamination of membranes produced by micromolding and soft lithography. B) Pourous PLGA structure formed by solvent casting and particulate leaching.

Once the membranes were fabricated, three-dimensional structures were assembled by stacking the layers together under an optical microscope using a pair of tweezers and then laminating them as described in the Examples. An example of one such structure is shown in FIG. 6A.

Any of the soft lithography methods above can be modified to produce porous PLGA molded membranes. Porous membranes were easily obtained using all of the soft lithographic methods. The only requirement was that the solution viscosity be low enough so that it can fill the mold evenly, and that the glucose grains be homogeneously mixed. An example of a microporous pattern obtained using micromolding is shown in FIG. 6B. Porous membranes are ideal/preferred for tissues that require ingrowth, vascularization, host integration, controllable degradation, or a reduction of polymer content.

Figure 7:
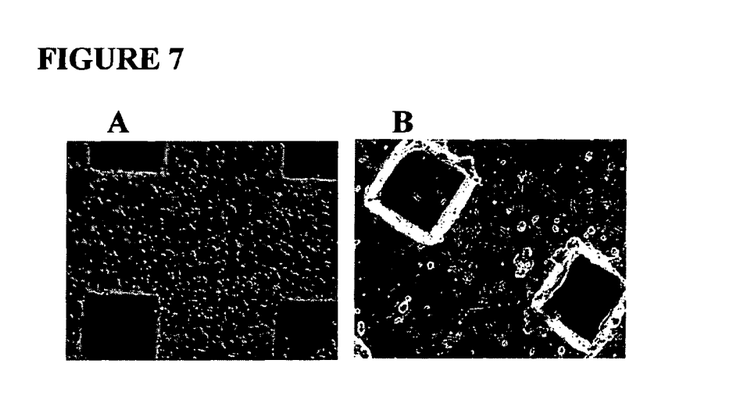
FIG. 7. Adhesion of A) primary hepatocytes and B) fibroblasts on PLGA scaffolds with microscale features.

Hepatocytes, and fibroblasts were seeded on scaffolds having similar line width but created using the various methods described herein (FIG. 7). In all cases, cell attachment and spreading was observed by light microscopy. Cells were maintained on the scaffolds for 2 weeks and were found to be viable by measures of cellular synthetic products in the media (e.g. albumin) and DNA.

Simple, robust microfabrication techniques for the construction of model two and three dimensional polymer scaffolds are taught to enable fundamental tissue engineering studies and in the development of scaffolds for artificial organs. The three soft lithography methods based on the common principle of casting biopolymers on PLGA scaffolds. PLGA scaffolds were fabricated as a prototypic polymer scaffold for tissue engineering. However, such scaffolds may also be used for forming miniaturized tissues for drug development & high-throughput screening, for controlling the differentiation of stem cells by altering the the characteristics of the microenvironmental 'niche.' The exact selection of polymer is a matter of choice and is within the ability of those skilled in the art. The specific end use of the scaffolds and the polymer selected for fabrication of the scaffold are not limitations of the invention. Applications of this technology in tissue engineering were explored by forming multilayer scaffolds, porous scaffolds, and by demonstrating adhesion of a number of cell types. These techniques can be used to study the effect of scaffold architecture on cellular activities such as proliferation, differentiation, motility, and therapeutic efficacy.

Example 1

Micromolding of PLGA Scaffolds

The micromolding technique is essentially solvent-casting on a PDMS mold. Many PLGA scaffolds can be produced with a single PDMS mold. The thickness of the resulting PLGA scaffold is determined by the height of the features on the photolithographic master (~30 microns in this example) and by the concentration of polymer in the solution. The feature height on the master can in principle be a few microns. However, thin membranes are fragile and are difficult to manipulate manually. It was empirically noted that scaffold heights of greater than ~30 microns yielded a scaffold with sufficient integrity to manipulate. The optimal PLGA concentration for use with this method was found to be around 10%-15%. At this concentration, the viscosity is high enough (around 100 cp) to allow the polymer solution to permeate the trenches of the PDMS mold when placed under vacuum. It was also observed that the solvent caused the PDMS mold to swell slightly. This limited the lateral resolution to a practical minimum of about 20-30 microns. Finally, it was observed that the polymer solution created menisci around each feature resulting in a surface that was not entirely flat. FIG. 5A shows an example of a micro-molded PLGA membrane with a line width of 50 microns and the size of the open square region being 300 microns on a side. Layers can be assembled into higher order structures as detailed below.

Example 2

Microfluidic Molding

The second variation was based on microfluidic flow. This technique took advantage of the microchannels created when a PDMS mold was reversibly sealed to a substrate. Microchannels were filled with a PLGA solution by application of negative pressure. In theory, the resolution of this technique is only limited by the resolution of the PDMS mold and hence the master. Practically, we found it difficult to mold patterns with small channel dimensions because the negative pressure that must be applied to fill the channels was excessive. Once the PLGA was cured, the PDMS was carefully removed to avoid damaging the thin structures. The average height of the scaffolds we fabricated was 10 microns. An typical scaffold obtained using this technique is shown in FIG. 5B. Unlike the other methods, microfluidic patterning could not be used to fabricate three dimensional structures because the polymer solution adhered strongly to the underlying substrate and could not be peeled off.

Example 3

Spin Coating

This method utilized a photoresist spin-coater to create a polymer layer that was thinner than the features on the master. A 5% PLGA solution was optimal for this method because the time required to fill the mold was compatible with the spinning time (~30 seconds). Highly viscous solutions did not completely fill the mold because the solvent evaporated during spinning before the polymer solution could permeate the PDMS structure. With a fixed polymer concentration, the height of the scaffold can be regulated by varying the spinning speed. Typically, a speed of 2000 rpm yielded membranes with an average height of 7 microns. A typical scaffold produced using this method is shown in FIG. 5C. Meniscus effects were observed in regions where the polymer was in contact with the hydrophobic PDMS mold, producing non-uniform scaffold heights. Additionally small holes were observed on the membrane surfaces and hypothesize that bubbles were introduced through rapid solvent escape. A practical minimum lateral feature size was found to be about 100 microns. Smaller line widths could not be achieved because the polymer solution was not able to fill the narrow microchannels during the spinning process. Membranes composed of large open areas from the mold were more difficult to remove. Layers may be assembled into higher order structures as detailed below.

Example 4

Multilayer Lamination

Once several two-dimensional PLGA membranes had been fabricated, it was possible to construct multilayer structures by laminating them together. This was accomplished by stacking membranes on top of each other under an optical microscope and clamping the edges of the layered scaffolds and heating for 10 minutes at 40° C. Alternatively, layers can be adhered to each other with PDMS or by application of a thin layer of solvent.

Example 5

Introduction of Porosity by Particulate Leaching

In conjunction with any of the membrane fabrication techniques described above, it is also possible to create scaffolds with an internal microstructure. This was accomplished by mixing 20-65 micron glucose grains, which had been previously minced and sieved, with the polymer solution in a 1:1 weight ratio. Any of a number of particles can be used as discussed above. To ensure that the polymer solution with glucose completely filled the mold, it was important that the solution not be too viscous. The optimum concentration of the polymer solution for this application was found to be around 5-10%. After the membrane was fabricated, the glucose particulates were removed by leaching in deionized water overnight.

Example 6

Cell Adhesion

Two and three dimensional PLGA scaffolds created using the methods of the invention were tested to demonstrate cell adhesion. Experiments were conducted on individual membranes with 200 micron features using primary hepatocytes, endothelial cells, and a fibroblast cell line (NIH 3T3). Hepatocytes were isolated from 2-3-month-old adult female Lewis rats as previously described (Bhatia et al, 1999). Routinely, 200-300 million cells were isolated with viabilities between 85% and 95%, as judged by trypan blue exclusion. Hepatocyte culture medium is composed of DMEM, supplemented with fetal bovine serum, insulin, glucagon, hydrocortisone, penicillin, and streptomycin. Fibroblasts were cultured using methods well known to those skilled in the art. Fibroblast culture medium consists of DMEM (Gibco, Grand Island, N.Y.) with glucose, supplemented with bovine calf serum (BCS, JRH Biosciences, Lenexa, Kans.), penicillin, and streptomycin.

Before seeding cells, all samples were placed under a vacuum for one week to ensure that there were no traces of solvent in the polymer. The scaffolds were sterilized by rinsing with 70% ethanol followed by copious amounts of sterile water, and finally placed under UV light for 10 minutes on each side. Three-dimensional laminated structures were subject to more rigorous washing with ethanol and water under a vacuum for 3 to 4 days. All samples were equilibrated with serum-free medium for an hour and then treated with a 0.1% (w/w) solution of collagen in PBS for one hour before seeding. The seeding density was $10^6$ cells/ml. Cells attached to scaffolds were photographed using phase contrast microscopy (FIG. 7)

Example 7

Coating of Scaffolds with Adhesion Molecules

Scaffolds can be coated homogeneously with a single factor (e.g. collagen) by placing the scaffold in the desired solution for sufficient time to allow for adsorbtion of the solution. It is possible to adsorb different factors onto individual layers prior to lamination into a three-dimensional scaffold to allow for preferentail binding sites for various cell types or to provide a gradient of growth factors, cytokines or other signaling molecules. Depending on the stability of the components to be adsorbed to the scaffold, two-dimensional scaffold layers may need to be adhered to each other with PDMS rather than by clamping and heating. More complex methods can be used to attach various factors to select portions of the scaffold. Such methods are well known to those skilled in the art and include, but are not limited to, covalent coupling of growth factors, chemokines and specific ECM components to the scaffold, the use of comb polymers (U.S. Pat. No. 6,399,700) and the direct application of factors to only discrete locations of the scaffold—including agents that repel cell adhesion (e.g. pluronics, surfactants, bovine serum albumin). Furthermore, the use of triblock polymers, such as pluronics, that have been modified with specific adhesive peptides or proteins may be utilized to selectively coat the scaffolds. Such methods are well known to those skilled in the art. Scaffolds may also be covalently modified with adhesive or repellant chemistries as described in Hermanson (1996).

Although an exemplary embodiment of the invention has been described above by way of example only, it will be understood by those skilled in the field that modifications may be made to the disclosed embodiment without departing from the scope of the invention, which is defined by the appended claims.

REFERENCES

Bhatia S N, and Chen C (1999) *Tissue Engineering at the Micro-Scale*, Biomedical Microdevices 2:131-144.
Bhatia, S. N., Balis U, Yarmush M L, and Toner M, Effect of Cell-Cell interactions in preservation of cellular phenotype: Co-Cultivation of Hepatocytes and Non-Parenchimal Cells, FASEB J, (1999), 13(14): p. 1883-1990.
Borenstein J. T., Terai H, King K. R., Weinberg E. J., Kaazempur-Mofrad M. R., and Vacanti J. P. Microfabrication Technology for Vascularized Tissue Engineering. Biomedical Microdevices, 2002 (4:3) p 167-175.
Chu T M, Orton D G, Hollister S J, Feinberg S E, and Halloran J W. (2002) Mechanical and in vivo performance of hydroxyapatite implants with controlled architectures. *Biomaterials*, 23:1283-1293.
Hermanson, G. T. (1996) *Bioconjugate Techniques*. Academic Press.

Kapur R, Spargo B J, Chen M S, Calvert J M, Rudolph A S (1996) Fabrication and selective surface modification of 3-dimensionally textured biomedical polymers from etched silicon substrates, *J Biomed Mater Res.* 33:205-16.

Mikos A. G., Sarakinos G., Leite S. M., Vacanti J. P., Langer R. (1993) Laminated three-dimensional biodegradable foams for use in tissue engineering, *Biomaterials* 14:323-330

Mrksich, M., et al., (1997) Using microcontact printing to pattern the attachment of mammalian cells to self-assembled monolayers of alkanethiolates on transparent films of gold and silver. *Experimental Cell Research* 235: 305-13.

Park A, Wu B, Griffith L G (1998) Integration of surface modification and 3D fabrication techniques to prepare patterned poly(L-lactide) substrates allowing regionally selective cell adhesion, *J Biomater Sci Polym Ed.* 9:89-110.

Shastri V P, Martin I, Langer R. (2000), Macroporous polymer foams by hydrocarbon templating. *Proc Natl Acad Sci USA.* 97:1970-5.

Zein I, Hutmacher D W, Tan K C, Teoh S H. (2000) Fused deposition modeling of novel scaffolds architectures for tissue engineering applications. *Biomaterials* 23:1169-1185

Zhao B., Moore J. S., Beebe D. J. (2001) Surface-directed liquid flow inside microchannels. *Science* 291:1023

We claim:

1. A layered polymer scaffold comprising a plurality of synthetic biopolymer membranes of from 30 micron to 1 millimeter in thickness, wherein said membranes comprise patterned through-holes having lateral dimensions of about 300 microns, with intervening biopolymer areas having a lateral feature width of about 50 microns, wherein said patterned through holes have lateral dimensions significantly greater than the lateral feature width of the intervening biopolymer areas, wherein said scaffold is microfabricated by a process comprising:
   generating an elastomer mold the approximate size of a silicon wafer;
   directing a synthetic biopolymer into the mold using a vacuum;
   curing the synthetic biopolymer in the mold to form a membrane of the plurality of synthetic biopolymer membranes, wherein said membrane comprises the patterned through-holes with intervening biopolymer areas, formed from the synthetic polymer by the microfabrication process;
   removing said membrane from the mold; and
   laminating said membranes to provide the layered polymer scaffold.

2. The polymer scaffold of claim 1, wherein the elastomer is selected from the group consisting of a silicone polymer, a poly(dimethylsiloxane) (PDMS) and an epoxy polymer.

3. The polymer scaffold of claim 1, wherein the synthetic biopolymer is selected from the group consisting of poly(L-lactic acid; PLLA); poly(DL-lactic acid; PLA); poly(DL-lactic-co-glycolic acid); PLGA and copolymers and blends thereof.

4. The polymer scaffold of claim 1, wherein the membranes are rendered porous by contacting the synthetic biopolymer with a particulate leaching agent.

5. The polymer scaffold of claim 4, wherein the particulate leaching agent is selected from the group consisting of a sugar, a salt and a protein.

6. The polymer scaffold of claim 1, wherein the step of laminating comprises attachment of the two or more cured polymer membranes to each other by applying mechanical pressure and heating.

7. A composition comprising the polymer scaffold of claim 1, wherein the polymer membranes are contacted with cells.

8. A three-dimensional, layered polymer structure comprising a plurality of synthetic biopolymer scaffolds of from 1 micron to 20 microns in thickness wherein said scaffolds comprise patterned through-holes with intervening biopolymer areas having a lateral feature width of at least about 100 microns, wherein said patterned through holes have lateral dimensions significantly less than the lateral feature width of the intervening biopolymer areas, wherein said scaffold is microfabricated by a process comprising:
   generating an elastomer mold the approximate size of a silicon wafer;
   directing a synthetic biopolymer into the mold by spin-coating the biopolymer onto the mold;
   curing the synthetic biopolymer in the mold to form a membrane of the plurality of synthetic biopolymer membranes, wherein said membrane comprises the patterned through-holes with intervening biopolymer, formed from the synthetic biopolymer by the microfabrication process;
   removing said membrane from the mold; and
   laminating said scaffolds to provide the three-dimensional layered polymer structure.

9. The polymer scaffold of claim 8, wherein the elastomer is selected from the group consisting of a silicone polymer, a poly(dimethylsiloxane) (PDMS) and an epoxy polymer.

10. The polymer scaffold of claim 8, wherein the synthetic biopolymer is selected from the group consisting of poly(L-lactic acid; PLLA); poly(DL-lactic acid; PLA); poly(DL-lactic-co-glycolic acid); PLGA and copolymers and blends thereof.

11. The polymer scaffold of claim 8, wherein the membranes are rendered porous by contacting the synthetic biopolymer with a particulate leaching agent.

12. The polymer scaffold of claim 11, wherein the particulate leaching agent is selected from the group consisting of a sugar, a salt and a protein.

13. The polymer scaffold of claim 8, wherein the step of comprises attachment of the two or more cured polymer membranes to each other by applying mechanical pressure and heating.

14. The polymer scaffold of claim 8, the wherein the polymer membranes are contacted with cells.

15. The polymer scaffold of claim 1, wherein the through-holes are squares and wherein the intervening biopolymer membrane is in the form of lines.

16. The polymer scaffold of claim 8, wherein the through-holes are squares and wherein the intervening biopolymer membrane is in the form of lines.

* * * * *